United States Patent [19]

Pawson

[11] Patent Number: 5,352,660
[45] Date of Patent: Oct. 4, 1994

[54] METHOD FOR ASSAYING FOR A SUBSTANCE THAT AFFECTS A SH2-PHOSPHORYLATED LIGAND REGULATORY SYSTEM

[75] Inventor: Anthyony J. Pawson, Toronto, Canada

[73] Assignee: Mount Sinai Hospital Corporation, Toronto, Canada

[21] Appl. No.: 786,057

[22] Filed: Oct. 31, 1991

[51] Int. Cl.$^5$ .................. A61K 37/02; G01N 33/566; C12Q 1/48; C07K 13/00
[52] U.S. Cl. ......................................... 514/12; 514/7; 436/501; 435/4; 435/7.1; 435/7.8; 435/15; 530/350; 530/352
[58] Field of Search .................. 435/4, 15, 7.1, 7.8; 530/350, 352; 514/7, 12; 436/501

[56] References Cited

U.S. PATENT DOCUMENTS 5,100,661  3/1992  Schmidt ........................... 424/85.8

OTHER PUBLICATIONS

Matsuda, M. et al. "Identification of Domains of the v-crk Oncogene Product Sufficient for Association with Phosphotyrosine Containing Proteins," Mol. Cell. Biol. 11(3) 1607–1613 (Mar. 1991).
Hanks, Proc. Nat. Acad. Sci. U.S.A. 84:388 (1987).
Wilks, Proc. Nat. Acad. Sci. U.S.A. 86:1603 (1989).
Pawson and Bernstein, Trends Gen. 6, 350 (1990).
Moran et al. Proc. Nat. Acad. Sci. U.S.A. 87:8622 (1990).
Anderson et al. Science 250:979 (1990).
Ellis et al Nature 343:377 (1990).
Ellis et al., Oncogene 6:895 (1991).
Moran et al., Mol. Cell. Biol. 11:1804 (1991).
Koch et al., Science 252:668 (1991).
Sadowski et al., Mol. Cell. Biol. 6, 4396 (1986).
Hunter and Cooper, Annu. Rev. Biochem. 54, 897 (1985).
Sun et al., Nature 352:73, 1991.
Ullrich and Schlessinger, Cell 61, 203 (1990).
Chen et al., Nature 328, 820 (1987).
Honneger, Mol. Cell. Biol. 7, 4568 (1987).
William, Science 243, 1564 (1989).
Yarden and Schlessinger, Biochemistry 26, 1434 (1987).

(List continued on next page.)

Primary Examiner—Robert A. Wax
Assistant Examiner—Rebecca Prouty
Attorney, Agent, or Firm—Bereskin & Parr

[57] ABSTRACT

A method for assaying a medium for the presence of a substance that affects an SH2-phosphorylated ligand regulatory system. The method employs an SH2-like domain or a subdomain thereof and a phosphorylated ligand. The phosphophorylated ligand is capable of interacting with the SH2-like domain or a subdomain thereof to form an SH2-phosphorylated ligand complex. The SH2-like domain or subdomain and/or the phosphorylated ligand are present in a known concentration. The SH2-like domain or a subdomain thereof and the phosphorylated ligand are incubated with a substance which is suspected of affecting an SH2-phosphorylated ligand regulatory system. The method is carried out under conditions which permit the formation of the SH2-phosphorylated ligand complex. SH2-phosphorylated ligand complex, free SH2-like domain or subdomains thereof, or non-complexed phosphorylated ligand are assayed. The invention also relates to an isolated SH2-phosphorylated ligand complex; a method of using an isolated SH2-like domain or a subdomain thereof to screen for phosphorylated ligands which are active in an SH2-phosphorylated ligand regulatory system; a method of using an isolated SH2-like domain or a subdomain thereof to regulate the interaction of a signalling protein with a related phosphorylated ligand; and a pharmaceutical composition comprising an isolated SH2-like domain or a subdomain thereof for use as an agonist or antagonist of the interaction of a signalling protein with a related phosphorylated ligand.

11 Claims, 10 Drawing Sheets

OTHER PUBLICATIONS

Böni-Schnetzler and Pilch. Proc. Natl. Acad. Sci. U.S.A. 84, 7832 (1987).
Heldin et al., J. Biol. Chem. 264, 8905 (1989).
Kazlauskas and Cooper, Cell 58, 1121 (1989).
Coughlin et al., Science 243, 1191 (1989).
Kazlauskas et al., Science 247, 1578 (1990).
Pawson, Oncogene 3, 491 (1988).
Veillette et al., Cell 55, 301 (1988).
Rudd et al., Proc. Natl. Acad. Sci. U.S.A. 85, 5190 (1988).
Shaw et al., Cell 59, 627 (1989).
Kypta et al., Cell 62, 481 (1990).
Ralston and Bishop, Proc. Natl. Acad. Sci. U.S.A. 82, 7845 (1985).
Gould and Hunter, Mol. Cell. Biol. 8, 3345 (1988).
Margolis et al., Cell 57, 1101 (1989).
Meisenhelder et al., Cell 57, p. 1109 (1989).
Morrison et al., Cell 58, 649 (1989).
Morrison et al., Proc. Natl. Acad. Sci. U.S.A. 85, 8855 (1988).
Rhee et al., Science 244, 546 (1989).
Whitman et al., Nature 332, 644 (1988).
Kaplan et al., Cell 50, 1021 (1987).
Courtneidge and Heber, Cell 50, p. 1031 (1987).
Fukui and Hanafusa, Mol. Cell. Biol. 9, 1651 (1989).
Carpenter et al., J. Biol. Chem. 265, 19704 (1990).
Auger et al., Cell 57, 167 (1989).
Adari et al., Science 240, 518 (1988).
Cales, Nature (London) 332, 548 (1988).
Kazlauskas and Cooper, EMBO J. 9, 3279 (1990).
Mayer et al., Nature 332, 272 (1988).
Mayer and Hanafusa, Proc. Natl. Acad. Sci. U.S.A. 87, 2638 (1990).
Rodaway et al., Nature 342, 624 (1989).
Drubin et al., Nature 343, 288 (1990).

FIGURE 2

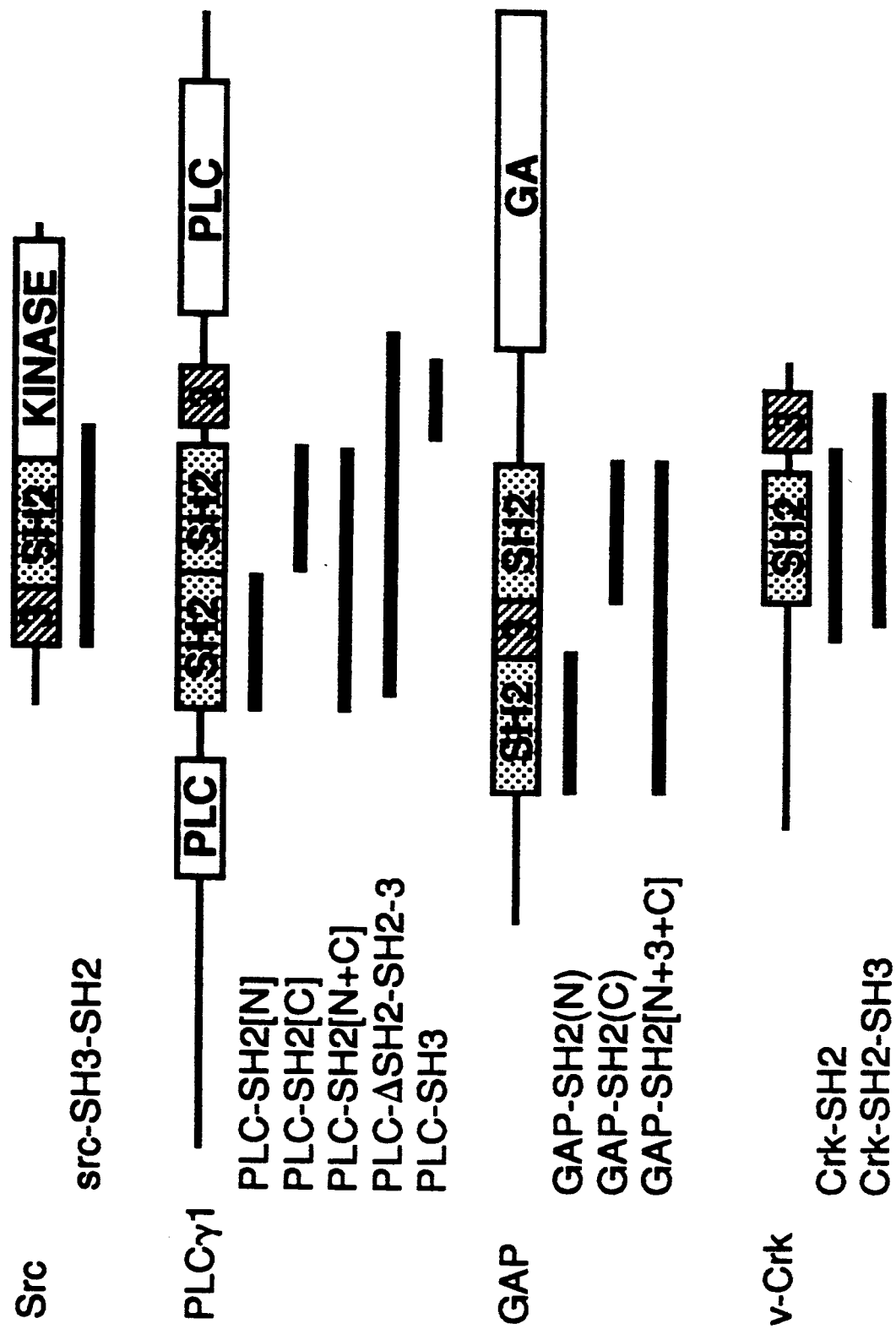

ns become physically associated with, and phosphorylated by, the activated PDGFR or EGF receptor (EGFR). A number of these receptor-binding proteins have been identified, including phosphoinositide-specific phospholipase C(PLC)-$\gamma$1 (Margolis et al, Cell 57 1101 (1989); Meisenhelder et al., ibid., p. 1109), p21$^{ras}$ GTPase-activating protein (GAP) (Kazlauskas et al., Science 247, 1578 (1990); Kaplan et al., ibid. 61, 121 (1990)), phosphatidylinositol (PI) 3'-kinase (PI3K) (Kazlauskas and Cooper, Cell 58, 1121 (1989); Coughlin et al., Science 243, 1191 (1989)), Src and Src-like tyrosine kinases (Kypta et al., Cell 62, 481 (1990)), and Raf (Morrison et al., ibid. 58, 649 (1989); Morrison et al., Proc. Natl. Acad. Sci. U.S.A. 85, 8855 (1988)). These associated proteins are likely targets of receptor activity.

METHOD FOR ASSAYING FOR A SUBSTANCE THAT AFFECTS A SH2-PHOSPHORYLATED LIGAND REGULATORY SYSTEM

FIELD OF THE INVENTION

The invention relates to a method for assaying a medium for the presence of a substance that affects an SH2-phosphorylated ligand regulatory system; an isolated SH2-phosphorylated ligand complex; a method of using an isolated SH2-like domain or a subdomain thereof to screen for phosphorylated ligands; a method of using an isolated SH2-like domain or a subdomain thereof to regulate the interaction of a signalling protein with a related phosphorylated ligand; and a pharmaceutical composition comprising an isolated SH2-like domain or a subdomain thereof.

BACKGROUND OF THE INVENTION

A common mechanism by which growth factors regulate cellular proliferation and differentiation is through transmembrane receptors with inducible protein-tyrosine kinase activity (Ullrich and Schlessinger, Cell 61, 203 (1990); Pawson and Bernstein, Trends Gen. 6, 350 (1990)). Indeed the mitogenic effects of growth factors such as epidermal growth factor (EGF) or platelet-derived growth factor (PDGF) absolutely require the tyrosine kinase activity of their receptors (Chen et al., Nature 328, 820 (1987); Honneger, Mol. Cell. Biol. 7, 4568 (1987); Williams, Science 243, 1564 (1989)). Growth factors induce receptors to cluster, which is followed by intermolecular tyrosine phosphorylation of the oligomerized receptors (Yarden and Schlessinger, Biochemistry 26, 1434 (1987); Böni-Schnetzler and Pilch, Proc. Natl. Acad. Sci. U.S.A. 84, 7832 (1987); Heldin et al., J. Biol. Chem. 264, 8905 (1989)). Autophosphorylation of the PDGF receptor (PDGFR) is important both for its subsequent interactions with substrates and for the induction of DNA synthesis (Kazlauskas and Cooper, Cell 58, 1121 (1989); Coughlin et al., Science 243, 1191 (1989); Kazlauskas et al., Science 247, 1578 (1990)).

A second group of tyrosine kinases, for which Src, Fps, and Abl are the prototypes, are entirely intracellular (Pawson, Oncogene 3, 491 (1988)). In the case of the Src-like tyrosine kinase Lck, which is specifically expressed in T cells, the NH$_2$-terminal region of the kinase associates with the short cytoplasmic tails of the cell adhesion molecules CD4 and CD8 (Veillette et al., Cell 55, 301 (1988); Rudd et al., Proc. Natl. Acad. sci. U.S.A. 85, 5190 (1988); Shaw et al., Cell 59, 627 (1989)). In addition, Src and the related kinases Fyn and Yes physically associate with, and are phosphorylated by, the $\beta$-PDGFR (Kypta et al., Cell 62, 481 (1990)). PDGF stimulation is associated with a three- to five-fold increase in Src kinase activity, which may serve to amplify the tyrosine kinase signal (Kypta et al., Cell 62, 481 (1990); Ralston and Bishop, Proc. Natl. Acad. Sci. U.S.A. 82, 7845 (1985); Gould and Hunter, Mol. Cell. Biol. 8, 3345 (1988)). Hence, the Src-like kinases also appear to participate in signal transduction.

Many structural alterations have been documented for both receptor-like and cytoplasmic tyrosine kinases, which induce constitutive tyrosine kinase activity and simultaneously activate oncogenic potential (Ullrich and Schlessinger, Cell 61, 203 (1990); Pawson and Bernstein, Trends Gen. 6, 350 (1990); Hunter and Cooper, Annu. Rev. Biochem. 54, 897 (1985)). The biological activities of transforming tyrosine kinases, like their normal counterparts, are generally dependent on their kinase activity.

After stimulation with PDGF or EGF several proteins become physically associated with, and phosphorylated by, the activated PDGFR or EGF receptor (EGFR). A number of these receptor-binding proteins have been identified, including phosphoinositide-specific phospholipase C(PLC)-$\gamma$1 (Margolis et al, Cell 57 1101 (1989); Meisenhelder et al., ibid., p. 1109), p21$^{ras}$ GTPase-activating protein (GAP) (Kazlauskas et al., Science 247, 1578 (1990); Kaplan et al., ibid. 61, 121 (1990)), phosphatidylinositol (PI) 3'-kinase (PI3K) (Kazlauskas and Cooper, Cell 58, 1121 (1989); Coughlin et al., Science 243, 1191 (1989)), Src and Src-like tyrosine kinases (Kypta et al., Cell 62, 481 (1990)), and Raf (Morrison et al., ibid. 58, 649 (1989); Morrison et al., Proc. Natl. Acad. Sci. U.S.A. 85, 8855 (1988)). These associated proteins are likely targets of receptor activity.

PLC-$\gamma$1 is one of several PLC isoforms that cleaves the phospholipid phosphatidylinositol 4,5-bisphosphate (PIP$_2$) to the second messengers diacylglycerol and inositol triphosphate, which in turn stimulate protein kinase C and raise intracellular calcium (Rhee et al., Science 244, 546 (1989)). PDGF stimulates PI turnover in cells where PLC-$\gamma$1 is the principal PLC isoform (Margolis et al., Cell 57, 1101 (1989); Meisenhelder et al., ibid., p. 1109), and overexpression of PLC-$\gamma$1 enhances the accumulation of inositol phosphates in response to PDGF (Margolis et al., ibid. 248, 607 (1990)). Thus, PLC-$\gamma$ may couple PDGF stimulation to the breakdown of PIP$_2$.

PI3K phosphorylates the inositol ring of PI in the D-3 position (Whitman et al, Nature 332, 644 (1988)). PI3K activity is associated with a variety of activated tyrosine kinases and correlates with the presence of a tyrosine phosphorylated 85-kilodalton (kD) protein (p85) (Kaplan et al., Cell 50, 1021 (1987); Courtneidge and Heber, ibid., p. 1031; Fukui and Hanafusa, Mol. Cell. Biol. 9, 1651 (1989)). Purified PI3K is a heterodimeric complex that contains p85 and a 110-Kd protein (p110) (Carpenter et al., J. Biol. Chem. 265, 19704 (1990)). The purified p85 subunit has no detectable PI3K activity, but binds tightly to activated PDGFR or EGFR in vitro. PDGF stimulation induces accumulation of PI-3,4-P$_2$ and PI-3,4,5-P$_3$, confirming that PI3K is regulated by tyrosine kinases in vivo (Auger et al., ibid. 57, 167 (1989)).

GAP stimulates the ability of p21$^{ras}$ (Ras) to hydrolyze GTP to GDP (guanosine diphosphate) (B. Margolis et al., ibid, 248, 607 (1990)) and thereby acts as a negative regulator by returning Ras from the active GTP-bound state to the inactive DGP-bound conformation. GAP interacts with the presumed effector region of p21$^{ras}$ (Adari et al., (1988) Science 240, 518–521; Cales, (1988) Nature (London) 332, 548–551) suggesting that it might also be the Ras target or might modify the association of p21$^{ras}$ with its target.

Raf is a protein-serine/threonine kinase that complexes with the PDGFR after PDGF stimulation, although it is unclear whether this is a direct interaction (Morrison et al., ibid. 58, 649 (1989); Morrison et al., Proc. Natl. Acad. Sci. U.S.A. 85, 8855 (1988)). In addition to these proteins, several unidentified polypeptides bind to activated PDGFR (Kazlauskas and Cooper, Cell 58, 1121 (1989); Coughlin et al., Science 243, 1191

(1989); Kazlauskas and Cooper, EMBO J. 9, 3279 (1990)).

The proteins that associate with activated growth factor receptors have quite distinct enzymatic properties and are structurally unrelated within their catalytic domains. However, with the exception of Raf they share conserved noncatalytic domains termed Src homology (SH) regions 2 and 3 (see FIG. 1 where 3 represents SH-3 domain; Ras GA the Ras GTPase activating region of GAP; PLC the catalytic sequences of PLC-γ1; gag, retroviral coat protein sequence; CYS, cysteine rich domain of Vav; LEU, leucine-rich region of Vav). The SH2 domain is a sequence of ~100 amino acids, originally identified in the vFps and vSrc cytoplasmic tyrosine kinases by virtue of its effects on both catalytic activity and substrate phosphorylation (T. Pawson, Oncogene 3, 491 (1988) and I. Sadowski et al., Mol. Cell. Biol. 6, 4396 (1986)).

An SH2 sequence has also been identified in the v-Crk oncoprotein, which complexes with several tyrosine phosphorylated proteins in crk-transformed cells (Mayer et al., Nature 332, 272 (1988); Mayer and Hanafusa, Proc. Natl. Acad. Sci. U.S.A. 87, 2638 (1990)). Most SH2-containing proteins also contain a motif, SH3, which is found independently in several cytoskeletal proteins and may mediate interactions with the cytoskeleton (Pawson, Oncogene 3, 491 (1988); Mayer et al., Nature 332, 272 (1988); Mayer and Hanafusa, Proc. Natl. Acad. Sci. U.S.A. 87, 2638 (1990); Rodaway et al., Nature 342, 624 (1989); Drubin et al., Nature 343, 288 (1990)).

SUMMARY OF THE INVENTION

The present inventors have determined by direct evidence that SH2 domains can mediate the interactions of diverse signalling proteins including cytoplasmic protein tyrosine kinases, p21$^{ras}$ GTPase-activating protein (GAP), phospholipase Cγ and the V-Crk oncoprotein, with a related set of phosphotyrosine ligands, including the epidermal growth factor (EGF) receptor. In particular, the present inventors found that in Src-transformed cells GAP forms heteromeric complexes, notably with a highly tyrosine phosphorylated 62-kDa protein (p62). The stable association between GAP and p62 can be specifically reconstituted in vitro by using a bacterial polypeptide containing only the N-terminal GAP SH2 domain. The efficient phosphorylation of p62 by the v-Src or v-Fps tyrosine kinases depends, in turn, on their SH2 domains and correlates with their transforming activity. In lysates of EGF-stimulated cells, the N-terminal GAP SH2 domain binds to both the EGF receptor and p62. Fusion proteins containing GAP or v-Crk SH2 domains complex with similar phosphotyrosine proteins from src-transformed or EGF-stimulated cells but with different efficiencies. SH2 sequences, therefore, form autonomous domains that direct signalling proteins, such as GAP, to bind specific phosphotyrosine-containing polypeptides. By promoting the formation of these complexes, SH2 domains are ideally suited to regulate the activation of intracellular signalling pathways by growth factors.

The inventors have most importantly found that the SH2 domains of cytoplasmic signalling proteins such as PLCγ1, GAP, Src and Crk are sufficient for in vitro binding to activated growth factor receptors. In particular, the inventors found that the SH2 domains of PLCγ1 synthesized individually in bacteria formed high affinity complexes with the epidermal growth factor (EGF)-or platelet derived growth factor (PDGF)-receptors in cell lysates, and bound synergistically to activated receptors when expressed together as one bacterial protein. In vitro complex formation was dependent on prior growth factor stimulation and was competed by intracellular PLCγ1. Similar results were obtained for binding of GAP SH2 domains to the PDGF-receptor. The isolated SH2 domains of other signalling proteins, such as p60$^{src}$ and Crk, also bound activated PDGF-receptors in vitro.

The use of a specialized non-catalytic domain to direct formation between protein kinases and their presumptive targets is unprecedented.

The finding that SH2 domains mediate the interactions of phosphorylated ligands with signalling proteins which regulate pathways that control gene expression, cell division, cytoskeletal architecture and cell metabolism permits the identification of substances which affect the interactions of phosphorylated ligands with signalling proteins and accordingly may be used in the treatment of conditions involving perturbation of signalling pathways. For example, it may be possible to identify substances which block an SH2-containing oncoprotein, or SH2 signalling protein or the actions of deregulated tyrosine kinases which interact with specific SH2 signalling proteins, and that may be useful in preventing transformation activity. In particular, in the case of cancers where there are deregulated tyrosine kinases, such as thyroid, breast carcinoma, stomach cancer and neuroblastoma, the method of the invention would permit the identification of substances which interfere with the binding of SH2 signalling proteins and the deregulated tyrosine kinase. In the case of cancers such as chronic myelogenous leukemia (CML) and acute lymphocytic leukemia (ALL), an SH2-containing oncoprotein interacts with a signalling protein which is autophosphorylated on serine resulting in transformation. The method of the present invention could be used to identify substances which interfere with the interaction and which may be useful in the treatment of CML and ALL.

Therefore, the present invention relates to a method for assaying a medium for the presence of a substance that affects an SH2-phosphorylated ligand regulatory system comprising providing an SH2-like domain or a subdomain thereof, and a phosphorylated ligand which is capable of interacting with said SH2-like domain or a subdomain thereof to form an SH2-phosphorylated ligand complex, said SH2-like domain or subdomain thereof and/or said phosphorylated ligand being present in a known concentration, and incubating with a substance which is suspected of effecting an SH2-phosphorylated ligand regulatory system, under conditions which permit the formation of said SH2-phosphorylated ligand complex, and assaying for said SH2-phosphorylated ligand complex, free SH2-like domain or subdomain thereof, or non-complexed phosphorylated ligand.

In a preferred embodiment of the invention, a method is provided for assaying a medium for the presence of an agonist or antagonist substance of an SH2-phosphorylated ligand regulatory system comprising providing an SH2-like domain or a subdomain thereof, and a phosphorylated ligand which is capable of interacting with said SH2-like domain or a subdomain thereof to form an SH2-phosphorylated ligand complex, said SH2-like domain or subdomain thereof and/or said phosphorylated ligand being present in a known concentration, and incubating with a suspected agonist or antagonist substance, under conditions which permit the formation of said SH2-phosphorylated ligand complex, and assaying for said SH2-phosphorylated ligand complex, free SH2-like domain or subdomains thereof, or non-complexed phosphorylated ligand.

The invention also provides a method for screening for antagonists that inhibit the effects of agonists of an SH2-phosphorylated ligand regulatory system. Thus, a substance that competes for the same binding site on the phosphorylated ligand or on the SH2-like domain or a subdomain thereof may be assayed.

The invention further provides an isolated SH2-phosphorylated ligand complex comprising an SH2-like domain or a subdomain thereof and a phosphorylated ligand which is capable of interacting with said SH2-like domain or a subdomain thereof.

The invention still further provides a method of using an isolated SH2-like domain or a subdomain thereof to screen for phosphorylated ligands which are active in an SH2-phosphorylated ligand regulatory system.

The invention also relates to a method of using an isolated SH2-like domain or a subdomain thereof to regulate the interaction of a signalling protein with a related phosphorylated ligand and a pharmaceutical composition comprising an isolated SH2-like domain or a subdomain thereof for use as an agonist or antagonist of the interaction of a signalling protein with a related phosphorylated ligand.

BRIEF DESCRIPTION OF THE DRAWINGS

The invention will be better understood with reference to the drawings in which:

FIG. 2 shows the amino acid sequences of several known SH2 domains;

FIG. 7 shows the locations of SH2 and SH3 domains in TrpE fusion proteins;

DETAILED DESCRIPTION OF THE INVENTION

Figure 1:
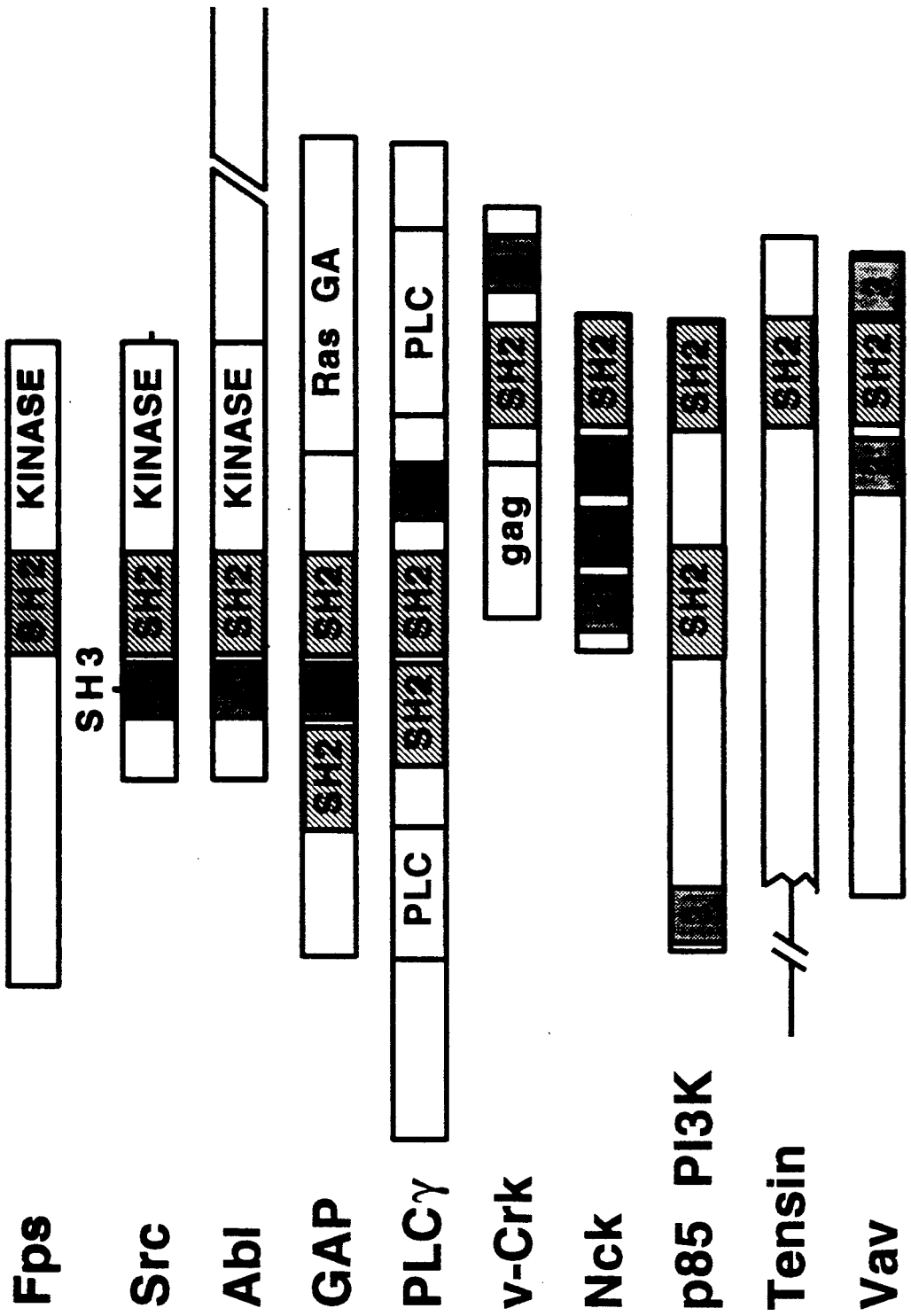
FIG. 1 shows the locations of SH2 domains of signalling proteins.

As hereinbefore mentioned the invention relates to a method for assaying a medium for the presence of a substance that effects an SH2-phosphorylated ligand regulatory system comprising providing an SH2-like domain or a subdomain thereof, and a phosphorylated ligand which is capable of interacting with said SH2-like domain or a subdomain thereof to form an SH2-phosphorylated ligand complex, said SH2-like domain or subdomain and/or said phosphorylated ligand being present in a known concentration, and incubating with a substance which is suspected of effecting an SH2-phosphorylated ligand regulatory system, under conditions which permit the formation of said SH2-phosphorylated ligand complex, and assaying for said SH2-phosphorylated ligand complex, free SH2-like domain or subdomains thereof, or non-complexed phosphorylated ligand.

In a preferred embodiment a method is provided for assaying a medium for the presence of an agonist or antagonist substance of an SH2-phosphorylated ligand regulatory system comprising providing an SH2-like domain or a subdomain thereof, and a phosphorylated ligand which is capable of interacting with said SH2-like domain or a subdomain thereof to form an SH2-phosphorylated ligand complex, said SH2-like domain or subdomain and/or said phosphorylated ligand being present in a known concentration, and incubating with a suspected agonist or antagonist substance, under conditions which permit the formation of said SH2-phosphorylated ligand complex, and assaying for said SH2-phosphorylated ligand complex, free SH2-like domain or subdomains thereof, or non-complexed phosphorylated ligand.

The invention further provides an isolated SH2-phosphorylated ligand complex comprising an SH2-like domain or a subdomain thereof and a phosphorylated ligand which is capable of interacting with said SH2-like domain or a subdomain thereof.

The invention still further provides a method of using an isolated SH2-like domain or a subdomain thereof to screen for phosphorylated ligands which are active in an SH2-phosphorylated ligand regulatory system.

The invention also relates to a method of using an isolated SH2-like domain or a subdomain thereof to regulate the interaction of a signalling protein with a related phosphorylated ligand and a pharmaceutical composition comprising an isolated SH2-like domain or a subdomain thereof for use as an agonist or antagonist of the interaction of a signalling protein with a related phosphorylated ligand.

The term "SH2-like domain or a subdomain thereof" refers to a sequence which is substantially homologous to a Src homology region 2 (SH2 region), or a subdomain of an SH region preferably a conserved region of an SH region. The Src homology region is a noncatalytic domain of ~100 amino acids which was originally identified in the Vfps and Vsrc cytoplasmic tyrosine kinases by virtue of its effects on both catalytic activity and substrate phosphorylation (T. Pawson, Oncogene 3, 491 (1988) and I. Sadowski et al., Mol. Cell. Biol. 6, 4396 (1986)). An SH2 sequence has also been identified in the v-Crk oncoprotein, which complexes with several tyrosine phosphorylated proteins in crk-transformed cells (Mayer et al., Nature 332, 272 (1988); Mayer and Hanafusa, Proc. Natl. Acad. Sci. U.S.A. 87, 2638 (1990)).

Figure 2:
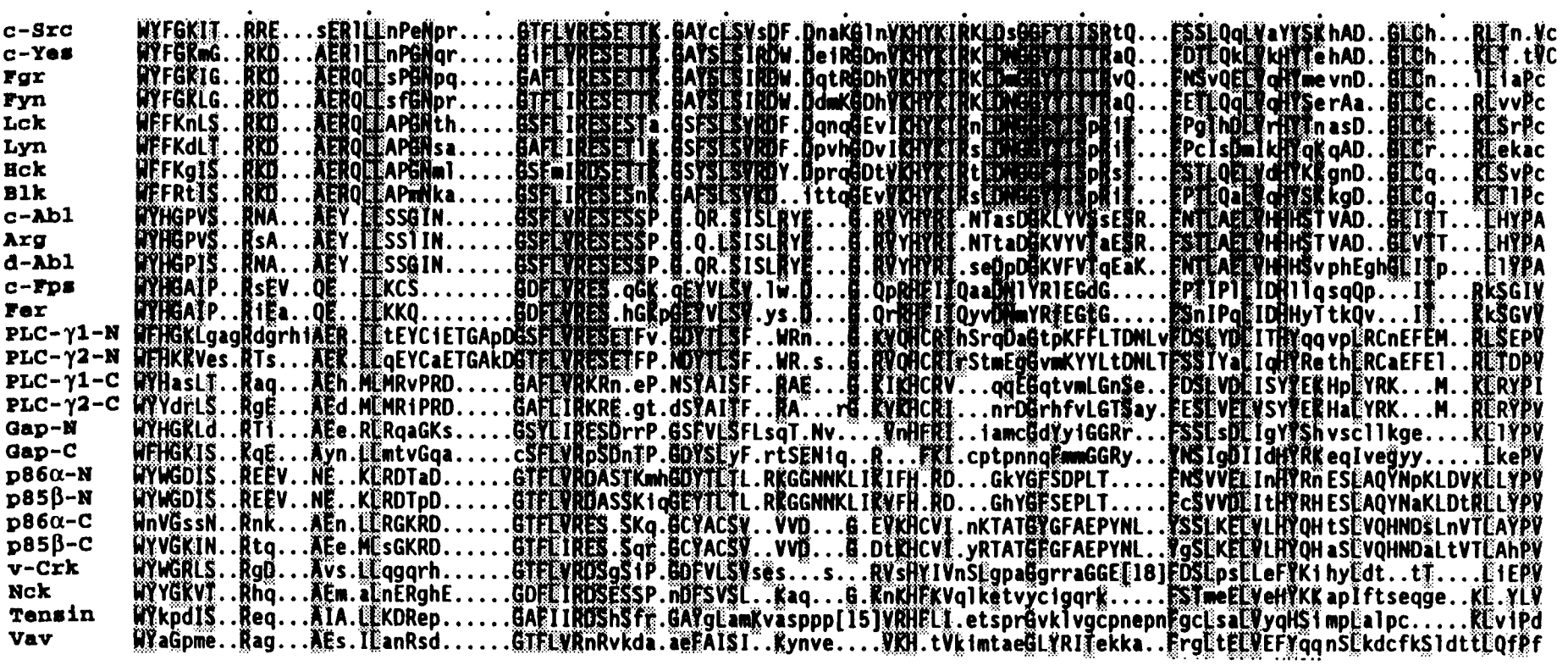

The sequences of several known SH2 domains are aligned in FIG. 2. In FIG. 2, residues that are conserved within at least three subfamilies of SH2 domains are capitalized and shaped. Residues that are conserved within one or two groups are capitalized. Residues that are poorly or not at all conserved are in lowercase. Invariant residues are indicated by asterisks. Conserved basic amino acids that might participate in interactions with phosphotyrosine are arrowed. Conserved motifs I to V are indicated by solid lines, whereas the connecting variable regions i to iv are indicated by broken lines. The suffix N indicates the more $NH_2$-terminal SH2 domain of PLC-γ, GAP or p85 whereas C indicates the more COOH-terminal domain. The SH2 domain of two isoforms of PLC-γ (γ1 and γ2) and p85 (α and β) are shown (Otsu et al., Cell 65, 91 (1991)). Sequences were aligned by eye. Abbreviations for the amino acid residues are: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

An inspection of the aligned SH2 sequences reveals the presence of five well-conserved sequence motifs (designated I to V in FIG. 2), which are separated by more variable sequence elements (i to iv). The variable regions generally contain one or more glycine or proline residues, suggesting that they form turns or hinges that connect the conserved subdomains.

The identification of SH2-like domains may be accomplished by screening a cDNA expression library with a phosphorylated ligand with high affinity to SH2 domains (e.g. the autophosphorylated COOH-terminal tail to the EGFR) to isolate cDNAs for SH2 proteins. One could use PCR (Wilks, A. F., Proc. Natl. Acad. Sci. U.S.A. Vol. 86, pp. 1603–1607, March 1989) or low stringency screening (Hanks, S. K., Proc. Natl. Acad. Sci. U.S.A. Vol. 84, pp 388–392, January 1987) with SH2 specific probe.

The term "phosphorylated ligand" refers to a polypeptide or peptide that is capable of interacting with an SH2-like domain or a subdomain thereof, and includes phosphotyrosine, and phosphoserine/phosphothreonine-containing peptides or polypeptides. Examples of ligands which may be utilized in the method of the invention are the SH2 binding sites on transmembrane receptors with inducible protein-tyrosine kinase activity and cytoplasmic tyrosine phosphorylated proteins.

It will be appreciated that the selection of an SH2-like domain or subdomain thereof and a phosphorylated ligand in the method of the invention will depend on the nature and expected utility of the substance to be assayed.

The phosphorylated ligand is preferably synthetically constructed having regard to the interaction of the phosphorylated ligand with a particular SH2 domain.

The term "SH2-phosphorylated ligand regulatory system" used herein refers to the interactions of an SH2-like domain or a subdomain thereof and a phosphorylated ligand and includes the binding of an SH2-like domain or a subdomain thereof to a phosphorylated ligand or any modifications to the SH2-like domain or a subdomain thereof or to the phosphorylated ligand associated therewith, to form an SH2/ligand complex thereby activating a series of regulatory pathways that control gene expression, cell division, cytoskeletal architecture and cell metabolism. Examples of such regulatory pathways are the GAP/Ras pathway, the pathway that regulates the breakdown of polyphosphoinositides through phospholipase C (PLC), and the Src/tyrosine kinase pathway.

The term "signalling protein" used herein includes cytoplasmic protein tyrosine kinases, $p21^{ras}$ GTPase-activating protein (GAP), phospholipase Cγ and the V-Crk oncoprotein, phosphatidylinositol (PI) 3'-kinase (PI3K), Src and Src-like tyrosine kinases, and Raf.

The invention may be used to assay for a substance that affects the interaction of an SH2-like domain or a subdomain thereof and a phosphorylated ligand, preferably a suspected agonist or antagonist. The agonist or antagonist may be an endogenous physiological substance or it may be a natural or synthetic drug.

The SH2-phosphorylated ligand complex, free SH2-like domain or subdomains thereof, or non-complexed phosphorylated ligand in the method of the invention may be isolated by conventional isolation techniques, for example, salting out, chromatography, electrophoresis, gel filtration, fractionation, absorption, polyacrylamide gel electrophoresis, agglutination, or combinations thereof.

The assaying for SH2-phosphorylated ligand complex, free SH2-like domain or subdomains thereof, or non-complexed phosphorylated ligand in the method of the invention may be carried out using known methods. To facilitate the assay of the components, antibody against the SH2-like domain or a subdomain thereof or the phosphorylated ligand, or a labelled SH2-like domain or a subdomain thereof, or a labelled phosphorylated ligand may be utilized.

The SH2 domain or subdomain thereof or phosphorylated ligand may be used to prepare monoclonal or polyclonal antibodies. Conventional methods can be used to prepare the antibodies. As to the details relating to the preparation of monoclonal antibodies reference can be made to Goding, J. W., Monoclonal Antibodies: Principles and Practice, 2nd Ed., Academic Press, London, 1986.

An SH2 domain or subdomain thereof or phosphorylated ligand may be labelled with various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include radioactive phosphorous $^{32}P$, iodine $I^{125}$, $I^{131}$ or tritium.

Radioactive labelled materials may be prepared by radiolabeling with $^{125}I$ by the chloramine-T method (Greenwood et al, Biochem. J. 89:114, 1963), the lactoperoxidase method (Marchalonis et al, Biochem. J. 124:921, 1971), the Bolton-Hunter method (Bolton and Hunter, Biochem. J. 133:529, 1973 and Bolton Review 18, Amersham International Limited, Buckinghamshire, England, 1977), the iodogen method (Fraker and Speck, Biochem. Biophys. Res. Commun. 80:849, 1978), the Iodo-beads method (Markwell Anal. Biochem. 125:427, 1982) or with tritium by reductive methylation (Tack et al., J. Biol. Chem. 255:8842, 1980).

Known coupling methods (for example Wilson and Nakane, in "Immunofluorescence and Related Staining Techniques", W. Knapp et al, eds, p. 215, Elsevier/North Holland, Amsterdam & New York, 1978; P. Tijssen and E. Kurstak, Anal. Biochem. 136:451, 1984) may be used to prepare enzyme labelled materials. Fluorescent labelled materials may be prepared by reacting the material with umbelliferone, fluorescein, fluorescein isothiocyanate, dichlorotriazinylamine fluorescein, dansyl chloride, derivatives of rhodamine such as tetramethyl rhodamine isothiocyanate, or phycoerythrin.

The SH2 domain or subdomain thereof or phosphorylated ligand used in the method of the invention may be insolubilized. For example, the SH2 domain or subdomain thereof or phosphorylated ligand may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc.

The insolubilized SH2 domain or subdomain thereof or phosphorylated ligand may be prepared by reacting the material with a suitable insoluble carrier using known chemical or physical methods, for example, cyanogen bromide coupling.

The invention also provides a method for screening for antagonists that inhibit the effects of agonists of an SH2-phosphorylated ligand regulatory system. Thus, a substance that competes for the same binding site on the phosphorylated ligand or on the SH2-like domain or a subdomain thereof is screened for.

It will be understood that the substances that can be assayed using the methods of the invention may act on one or more of the SH2-binding site on the phosphorylated ligand or the ligand-binding site on the SH2-like domain or subdomain thereof, including agonist binding sites, competitive antagonist binding sites, non-competitive antagonist binding sites or allosteric sites.

The following non-limiting examples are illustrative of the present invention:

EXAMPLES

The following materials and methods were utilized in the investigations outlined in Examples 1 and 2:

Antibodies

Polyclonal rabbit antibodies against human GAP residues 171–448 or phosphotyrosine were raised and affinity-purified, as described in Ellis, C. et al (1990) Nature (London) 343, 377–381 and Kamps, M. P. & Sefton; B. M. (1988) Oncogene 2, 305–315. Anti-trpE rabbit antiserum was raised against a 37 Kda protein containing the N-terminal 323 residues encoded by the Escherichia coli trpE protein. Affinity-purified rabbit anti-phosphotyrosine antibodies were prepared as described in Kamps, M. P. & Sefton, B. M. (1988) Oncogene 2, 305–315. Antibodies directed against a peptide corresponding to residues 1176–1186 of the human EGF-R (Honegger, A. M. et al., (1989) Proc. Natl. Acad. Sci. USA 86, 925–929) were utilized.

Cell Culture

Growth conditions, $^{32}Pi$ labeling, EGF treatment, and immunoprecipitation of R1hER (obtained from M. Weber, University of Virgina, Charlottesville), Rat-2, and Rat-2 cells expressing v-src or v-fps genes were as described in Declue, J. and Martin, G. S. (1989) J. Virol. 63, 542–554; Koch, V. A. et al. (1989) Mol. Cell. Biol. 9, 4131–4140; and Ellis, C. et al (1990) Nature (London) 343, 377–381.

Complex Formation with Bacterial trpE Fusion Proteins

Restriction fragments from human GAP, bovine PLC$\gamma$, or v-crk CDNAS were subcloned into PATH bacterial TrpE expression vectors, using both natural and engineered restriction sites (Ellis, C. et al (1990) Nature (London) 343, 377–381). Fifty ml cultures of E. coli RR1 with the parental PATH expression plasmid, or a derivative encoding one of the various TrpE fusion proteins were grown and induced with indole acrylic acid as described in Moran, F. et al (1988) Oncogene 3, 665–672. Cells were washed with 1 ml of 50 mM Tris-HCl, pH 7.5, 10% (wt./vol.) sucrose followed by a 2 minute centrifugation at 15,000×g. The cells were resuspended in 1 ml of ice-cold PLCLB (50 Mm HEPES, Ph 7.0/150 Mm NaCl/10% glycerol/1% Triton X-100/1.5 Mm MgCl$_2$/1 Mm EGTA/100 Mm NaF/10 Mm NaPP$_1$/1 Mm Na$_3$VO$_4$/1 Mm phenyl/methylsulfonyl fluoride/aprotinin and leupeptin each at 10 $\mu$g/ml) sonicated 6 times for 10 seconds each and clarified by centrifugation at 15,000×g for 15 minutes. Sonication and all subsequent steps were done at 4° C. Supernatants were incubated with 40 $\mu$l of anti-trpE serum and 30 $\mu$l of protein A-Sepharose beads. After being gently mixed for 90 minutes, the immune complexes were washed three times with HNTG buffer (20 Mm HEPES, Ph 7.0 150 Mm NaCl, 0.1% Triton X-100, 10% glycerol, 1 Mm Na$_3$VO$_4$) and divided into four equal aliquots. Similar amounts of the different TrpE fusion protein were detected in these immune complexes by immunoblotting with anti-TrpE antiserum.

For in vitro binding experiments, approximately 5×10$^6$ non-radioactive or $^{32}P$-labelled cells were lysed in 1 or 2 ml PLCLB and clarified as described below. One ml of clarified lysate was incubated with one aliquot of an anti-trpE immune complex. After mixing by gentle inversion for 90 minutes at 4° C., the immune complexes were recovered by centrifugation, washed three times with HNTG, resuspended in 40 $\mu$l of SDS sample buffer and heated at 100° C. for 3 minutes.

Immunoblotting

Cell lysates (prepared as in Koch, C.A. et al (1989) 9, 4131–4140; 25 $\mu$g of protein per lane), immunoprecipitates, and bacterial complexes were resolved by SDS-polyacrylamide gel electrophoresis and transferred to nitrocellulose in a semi-dry blotting apparatus at 0.8 Ma.cm$^{-2}$ for 60 minutes. Blots were analyzed by autoradiography ($^{32}P$-labelled samples) or were blocked and then probed with anti-EGFR antiserum (1:200 dilution) or antiphosphotyrosine antibodies as described in Koch, C.A. et al (1989) Mol. Cell. Biol. 9, 4131–4140. Anti-phosphotyrosine blots of whole-cell lysates were probed with 10 $\mu$Ci of $^{125}I$-labelled protein A (2–10 $\mu$Ci/$\mu$g; 1 Ci=37 GBg; New England Nuclear), whereas all other blots were probed with 5 $\mu$Ci of high-specific-activity $^{125}I$-labelled protein A (35 $\mu$Ci/$\mu$g, Amersham). Blots were exposed to Kodak XAR film at −75° C. with an intensifying screen.

EXAMPLE 1

Figure 3:
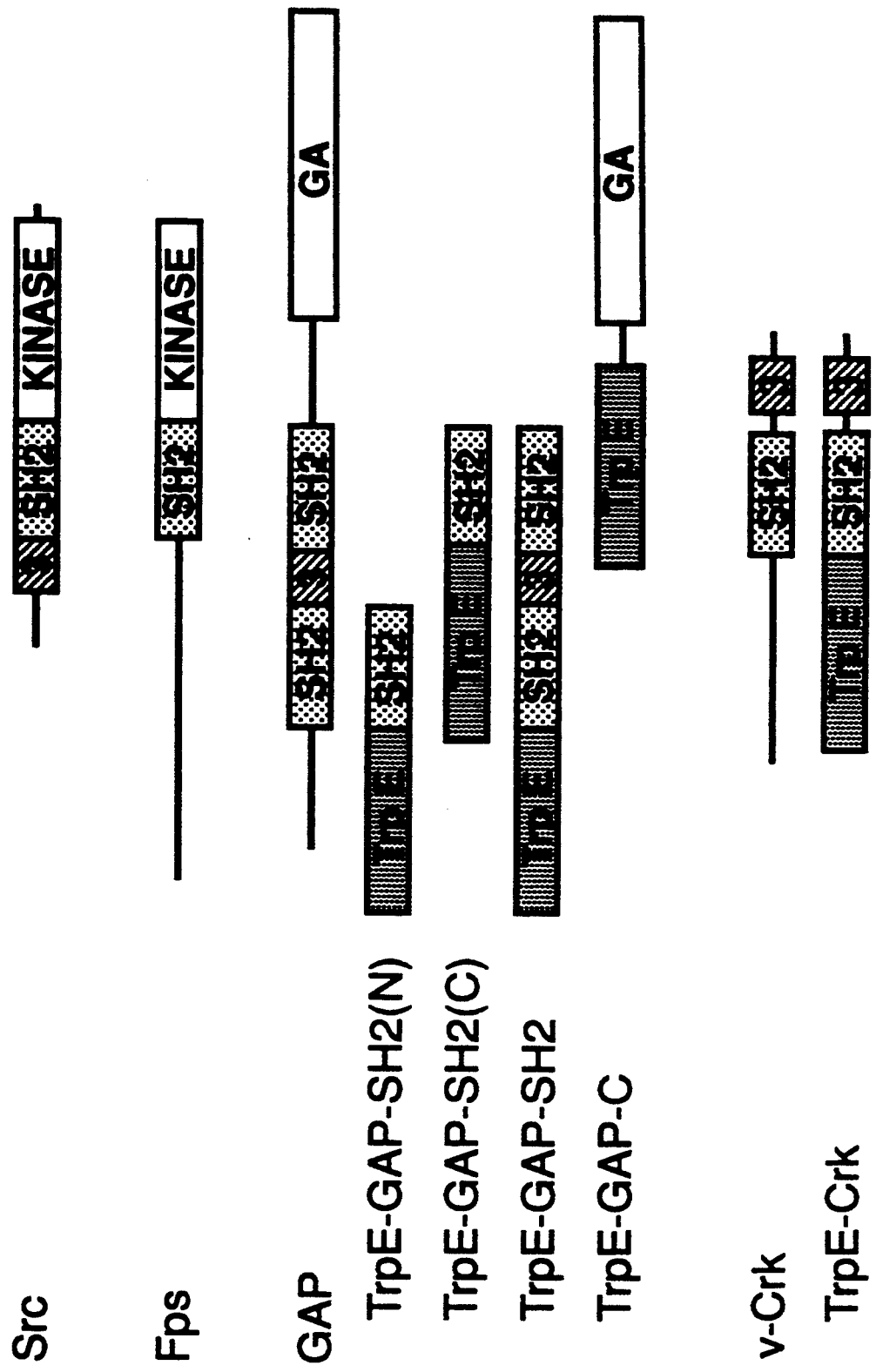
FIG. 3 shows the locations of SH2 and SH3 domains in signalling and transforming proteins and in TrpE fusion proteins.

GAP and Crk SH2 domains Bind a Related Set of Phosphotyrosine-containing Proteins The disposition of SH2 and SH3 domains within several signalling and transforming proteins is shown in FIG. 1. GAP was initially used to test whether these regions might be involved in protein-protein interactions. Different regions of GAP were expressed in bacteria as TrpE-GAP fusion proteins joined to a 37 -Kda TrpE protein (FIG. 3). The fusion proteins contained the following residues: TrpE-GAP-SH2, human GAP 171–448; TrpE-GAP-SH2(N), GAP 178–278; TrpE-GAP-SH2(C), GAP 348–445; TrpE-GAP-C, GAP 670–1047; TrpE-V-Crk, P47$^{gag\text{-}crk}$ 206–327; TrpE-PLC$\gamma$, bovine PLC$\gamma$1 956–1291.3=SH3 domain; GA=GTPase activating region of GAP.

TrpE-GAP-SH2 contains almost precisely the two GAP SH2 domains and the intervening SH3 sequences. In contrast, TrpE-GAP-C contains the C-terminal half of GAP, including all residues required to stimulate p21$^{ras}$ GTPase activity (Marshall, M. S. et al (1989) EMBO. J. 8, 1105–1110). As controls, the TrpE protein by itself and a TrpE-PLC$\gamma$ fusion protein containing C-terminal PLC$\gamma$ catalytic sequences were used. These TrpE fusion proteins were immunoprecipitated with anti-TrpE antiserum.

To investigate whether these polypeptides could form specific complexes with proteins from src-transformed cells, the immunoprecipitates were incubated with a lysate of Rat-2 v-src cells (FIG. 4A Lanes 5–8) and with lysates of normal Rat-2 fibroblasts (FIG. 4A Lanes 1–4) and analyzed for associated proteins by immunoblotting with anti-phosphotyrosine antibodies. Phosphotyrosine bound to TrpE-GAP-SH2 from Rat-2 v-src cells (Lane 9) were also compared directly with an anti-GAP immunoprecipitate from the same lysate (Lane 10).

Figure 4A:
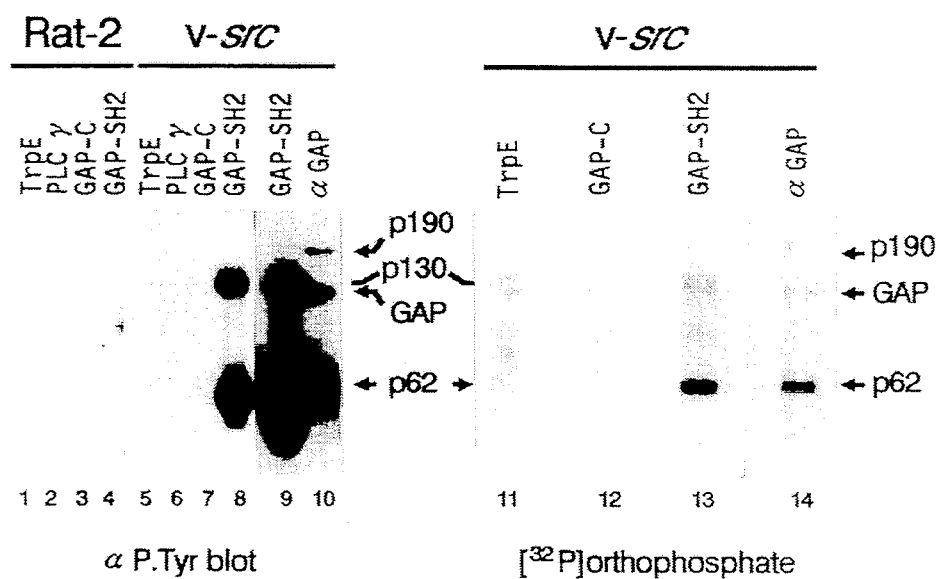
FIG. 4 shows the immunoblots and autoradiograms of TrpE fusion proteins that were mixed with lysates of normal Rat-2 cells of v-src transformed Rat-2 cells.

TrpE, TrpE-PLC$\gamma$ and TrpE-GAP-C which lack SH2 sequences, did not retain any phosphotyrosine-containing proteins from the Rat-2 v-src lysate. However, TrpE-GAP-SH2 bound a 62 KDA tyrosine phosphorylated protein, as well as variable amounts of a 130 Kda protein (FIG. 4A). The 62 Kda protein co-migrated with p62 immunoprecipitated with anti-GAP antibodies from Rat-2 v-src cells.

As a more direct test of their binding activities, the TrpE fusion proteins were incubated with lysate of Rat-2 v-src cells that had been metabolically labelled with $^{32}$P$_i$ (Lanes 11–13). A lysate from $^{32}$P$_i$-labeled Rat-2 v-src cells was also incubated with anti-GAP antibodies (Lane 14). Precipitated $^{32}$P labelled proteins were visualized by autoradiography (right panel). Exposure time was 3 hours, except for lane 14 (18 hours). Again, TrpE-GAP-SH2 specifically bound a 62 Kda phosphoprotein that comigrated with GAP-associated p62 (FIG. 4A). The same result was obtained using $^{32}$P-labelled v-fps-transformed cells. Tryptic phosphopeptide analysis confirmed the identity of the 62-Kda SH2-binding protein as p62. p62 is not obviously related to p60$^{src}$, and lacks detectable in vitro protein kinase activity. The 130 Kda protein that bound the TrpE-GAP-SH2 may correspond to a protein (p130) whose phosphorylation by activated p60$^{src}$ requires the Src SH2 domain, with which it complexes in vivo (Reynolds, A.B. et al. (1989) Mol. Cell. Biol. 9, 3951–3958 and Lau, A. F. (1986) Virology 151, 86–99).

Figure 4B:
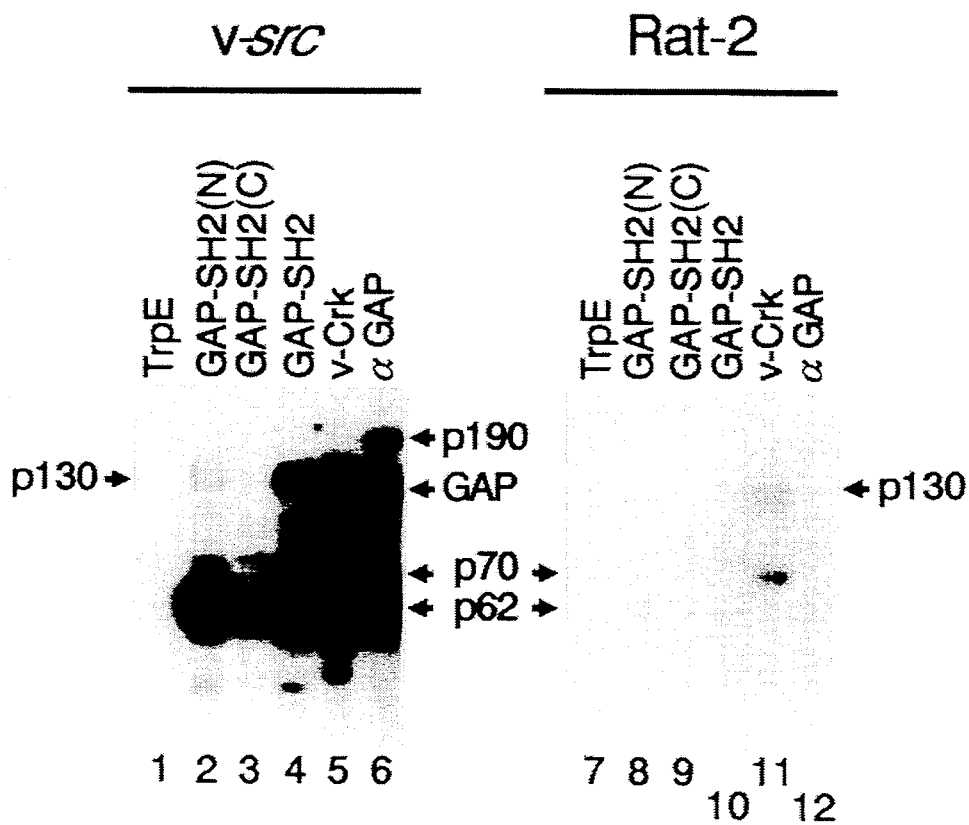

Immobilized TrpE (FIG. 4B), TrpE-GAP-SH2(N) (FIG. 4B), TrpE-GAP-SH2(C) (FIG. 4B), TrpE-GAP-SH2 (FIG. 4B) and TrpE-v-Crk (FIG. 4B) were incubated with lysates from Rat-2 v-src cells (FIG. 4B) or normal Rat-2 Cells (FIG. 4B). For comparison, anti-GAP immunoprecipitations (FIG. 4B) were made from the same cell lysates. Samples were analyzed by immunoblotting with anti-phosphotyrosine antibodies and $^{125}$I-Protein-A. Autoradiography was for 16 hours (lanes 1–6) or 3 days (lanes 7–14).

The binding sites for p62 and p 130 were more precisely ascribed to the N-terminal SH2 domain of GAP (GAP-SH2(N), FIG. 3) which efficiently bound p62 and p130 from Rat-2 v-src cells (FIG. 4B).

To investigate whether these tyrosine phosphorylated proteins might be more general ligands for SH2-containing proteins similar experiments were done with a TrpE-v-Crk fusion protein (FIG. 3). TrpE-v-Crk also bound two phosphotyrosine-containing proteins when incubated with a Rat-2 v-src lysate, which likely correspond to p62 and p130 (FIG. 4B). TrpE-v-Crk bound p130 more efficiently than did TrpE-GAP-SH2, and also associated with a distinct 70 kDa tyrosine phosphorylated protein (p70). In lysates of normal Rat-2 cells TrpE-GAP-SH2 bound a small amount of p62, whereas TrpE-v-Crk formed more readily detectable complexes with p130 and p70 (FIG. 4B). It is of interest that phosphotyrosine-containing proteins of this size are associated with P47$^{gag\text{-}crk}$ in v-crk-transformed chicken embryo fibroblasts, and bind bacterial v-Crk in lysates of v-crk-transformed cells (Mayer, B. J. et al (1988) Nature London) 332, 272–275; Mayer, B. J. et al (1988) (Cold Spring Harbor Symp. Quant. Biol. 53, 907–914; Mayer, B. J. & Hanafusa, H. (1990) Proc. Natl. Acad. Sci. U.S.A. 87, 2638–2642). These results indicate that the GAP and Crk SH2 domains have distinct but overlapping binding specificities. They bind common phosphotyrosine-containing ligands, but apparently with different efficiencies.

EXAMPLE 2

The N terminal GAP SH2 Domain Binds Activated EGF Receptor In Vitro.

GAP has been implicated in the response to growth factors such as epidermal growth factor (EGF) and platelet-derived growth factor (PDGR), and shown to form a physical complex with the PDGF-receptor. Therefore the binding activity of TrpE-GAP bacterial proteins in lysates of Rat-1 cells expressing the human EGF-receptor (EGF-R) ($\approx 2.5 \times 10^5$ per cell) was investigated.

Figure 5A:
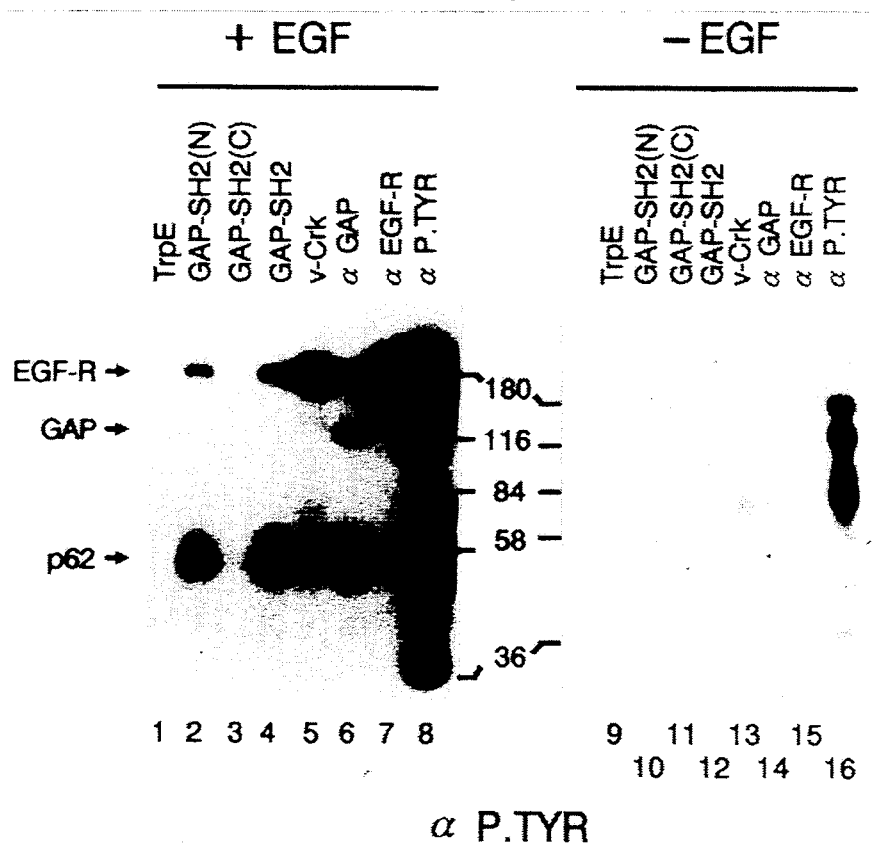
FIG. 5 shows the immunoblots of immobilized TrpE fusion proteins that were mixed with lysates of serum-starved Rat-1 cells overexpressing human EGFR that were stimulated with 0 or 80 nM EGF (A) and immunoblots with anti-EGFR antibodies of nitrocellulose filters containing duplicate samples of those in A (B)
Figure 5B:
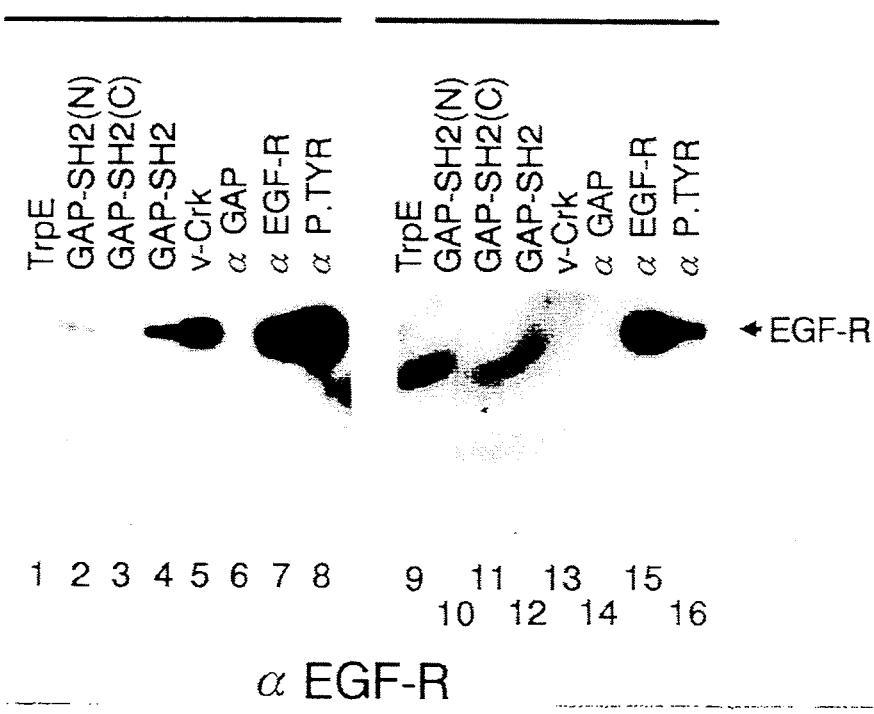

Serum-starved (for 48 hours) Rat-1 cells overexpressing human EGF-receptors were stimulated with 0 (FIG. 5 lanes 9 to 16), or with 80 nM EGF (lanes 1 to 8) for 5 minutes at 37° C. Cells lysates were mixed with the indicated TrpE bacterial fusion proteins, immunobilized with anti-TrpE antibodies (lanes 1–5,9–13), or immunoprecipitated with anti-GAP (lanes 6,14), anti-EGF-R (lanes 7,15) or anti-phosphotryosine (lanes 8,16) antibodies. Complexes and immunoprecipitates were washed and analyzed by western blotting with antiphosphotryosine antibodies. Nitrocellulose filters containing duplicate samples of those in were immunoblotted with anti-EGF-R antibodies (FIG. 5B).

No phosphotyrosine-containing proteins associated with immobilized TrpE fusion proteins before EGF stimulation (FIG. 5A), or with TrpE-GAP-C following addition of EGF. However, TrpE-GAP-SH2, TrpE-GAP-SH2(N) and TrpE-v-Crk precipitated two tyrosine phosphorylated proteins from lysates of EGF-stimulated cells, with mobilities of 62 and 180 kDa (FIG. 5A). The 62 kDa protein comigrated with p62 precipitated from the EGF-stimulated lysate with anti-GAP antibodies. The 180 kDa band comigrated with the EGF-R immunoprecipitated from the same lysate, was recognized by anti-EGF-R antibodies on an immunoblot (FIG. 5B), and was phosphorylated on tyrosine in an in vitro kinase reaction. These data show that the 180-kDa protein is the EGF-R and that its association with SH2 domains is clearly dependent on prior EGF stimulation (FIG. 5B). TrpE-v-Crk bound the EGF-R more effectively than the GAP SH2 fusion proteins, but was less efficient in p62-binding (FIGS. 5A and B, lane 5)

EXAMPLE 3

Fps and Src SH2 Domains Are Required for Tyrosine Phosphorylation of p62 and GAP p62 is rapidly and abundantly phosphorylated by activated v-Src and v-Fps tyrosine kinases (Ellis, C., et al. (1990) Nature (London) 343, 377–381). The v-Fps SH2 domain, and Glu-832 in particular have been previously implicated in recognition of a 62-kDa protein whose phosphorylation correlates with transformation (Koch, C. A. et al. (1989) Mol. Cell. Biol. 9, 4131–4140). Therefore, an investigation was carried out to determine whether this substrate corresponds to p62, which displays an affinity for SH2 domains in vitro (see Example 1). In particular, total cell lysates, or anti-GAP immunoprecipitates from Rat-2 cells expressing either wild type P130$^{gag\text{-}fps}$ (v-fps), or a glu$^{832}$→lys amino acid mutant (K-832) were analyzed by immunoblotting with anti-phosphotryosine antibodies.

Figure 6A:
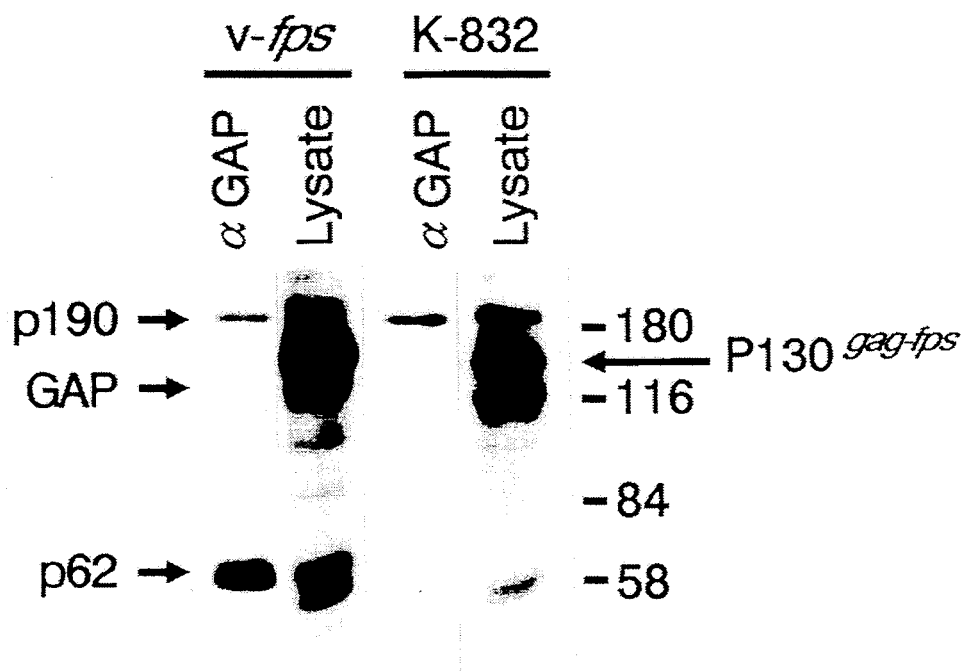
FIG. 6 shows immunoblots with anti-phosphotyrosine antibodies of total cell lysates, or anti-GAP immunoprecipitates from Rat-2 cells expressing either wild type P130$^{gag\text{-}fps}$ (v-fps), or mutant P130$^{gag\text{-}fps}$ with a glu$^{832}$→lys amino acid substitution in the SH2 domain (K-832) (A) and immunoblots with anti-phosphotyrosine antibodies of anti-GAP immunoprecipitates, or total cell lysates from Rat-2 cells expressing wt v-src, or the SRX5, SHX13 or XD6 v-src mutants, or containing empty vector.

Direct comparison revealed that GAP-associated p62, precipitated with anti-GAP antibodies from cells transformed by wild type (wt) v-fps, comigrated with the prominent SH2-dependent 62-kDa substrate identified in the whole cell lysate. Furthermore, little phosphotyrosine-containing p62 could be detected in anti-GAP immunoprecipitates from cells expressing a v-Fps mutant with a substitution of lysine for Glu-832 in the SH2 domain (FIG. 6A). GAP itself is a relatively poor substrate for P130$^{gag\text{-}Fps}$ (Ellis, C. et al. (1990) Nature (London) 343, 377–381); prolonged exposure revealed that GAP tyrosine phosphorylation also depends on the v-Fps SH2 domain.

A series of in-phase linker-insertion and deletion mutations constructed in v-src has yielded several mutants that have relatively high levels of p60$^{v\text{-}src}$ kinase activity, but are poorly transforming in Rat-2 cells (DeClue, J. & Martin, G. S. (1989) J. Virol. 63, 542–554). The XD6 and SHX13 mutants have alterations within highly conserved regions of the v-Src SH2 domain. XD6 has a deletion of residues 149–174, and the SHX 13 mutation inserts Arg-Ala after residue 228. In contrast, the SRX5 mutation replaces the codon for the tyr$^{416}$ autophosphorylation site in the catalytic domain with codons for Ser-Arg-Asp.

Figure 6B:
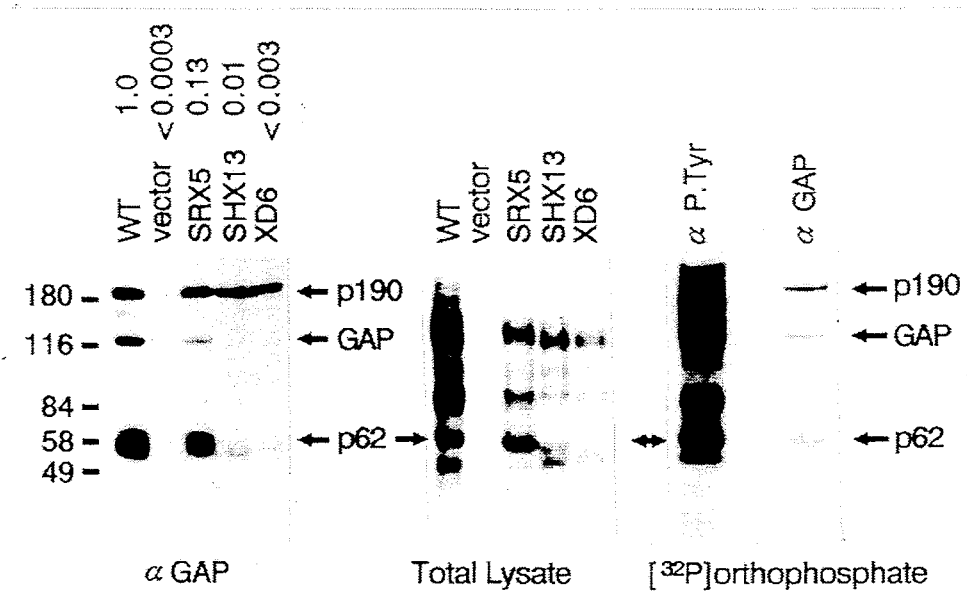

Anti-GAP immunoprecipitates (FIG. 6B, left panel), or total cell lysates (FIG. 6B, middle panel) from Rat-2 cells expressing wild type v-src, or the SRX5, SHX13 or XD6 v-src mutants, or containing empty vector, were analyzed by immunoblotting with anti-phosphotyrosine antibodies. The focus forming activities of the v-src mutants on Rat-2 cells relative to wt are indicated (DeClue, J. & Martin, G. S. (1989) J. Virol. 63, 542–554). In addition, Rat-2 v-src cells were metabolically labelled with $^{32}$Pi for 2 hours, followed by immunoprecipitation with anti-phosphotyrosine or anti-GAP antibodies. These immunoprecipitates were separated by gel electrophoresis, transferred to immunoblots and subjected to autoradiography (FIG. 6B, right panel).

Rat-2 cells expressing these v-src mutants contained similar levels of GAP and p60$^{v\text{-}src}$ compared with wild type v-src-transformed cells. However, anti-GAP immunoprecipitations showed that the tyrosine phosphorylation of GAP-associated p62, and of GAP itself, was greatly decreased in cells expressing the SHX13 and XD6 v-src SH2 mutants, correlating with their particularly low Rat-2 transforming activity (FIG. 6B). In contrast, the SRX5 autophosphorylation site mutant has an intact SH2 domain, retains 13% of wild type transforming activity on Rat-2 cells, and still gives appreciable phosphorylation of p62 and GAP. Unlike p62, which is minor but highly phosphorylated protein, p190 contains relatively little phosphotyrosine but it is a major GAP-binding protein (Ellis, C. et al (1990) Nature (London) 343,377–381). p190 tyrosine phosphorylation was not affected by the v-src or v-Fps SH2 mutations and hence, does not require the tyrosine kinase SH2 domain and does not correlate with transformation. Binding of tyrosine phosphorylated p190 to GAP SH2 domains or C-terminal region in vitro was not observed, possibly because all the available p190 is already associated with GAP in cell lysates.

EXAMPLE 4

SH2 domains of PLCγ1 synthesized in bacteria bind synergistically in vitro to activated EGF- and PDGF-receptors.

The following materials and methods were utilized in the example:

Restriction sites were introduced on either side of SH2 coding sequences in the cDNA's for bovine PLCγ1 and human GAP with oligonucleotide-directed mutagenesis (Kunkel, et al., Methods Enzymol. 154, 367 (1987)). For each individual SH2 domain an Sph I site was created at the 5' end and an Nhe I site at the 3' end. These Sph I-Nhe I fragments were cloned into a pATH bacterial trpE expression vector whose multiple cloning site had been modified to contain unique Sph I and Nhe I sites. For fusions that contained both SH2 domains, the Sph I site of the NH$_2$-terminal SH2 domain and the Nhe I site of the COOH-terminal SH2 domain were used for the excision, Src and Crk fusion proteins utilized natural restriction sites. The resulting fusion proteins contained the NH$_2$-terminal 323 amino acids of TrpE and retained the desired reading frame for PLCγ1 or GAP.

Cultures of E. coli RR1 with pATH expression plasmids were grown, induced, and lysed as described above in Example 1. The TrpE fusion proteins were recovered from the supernatants by immunoprecipitation with polyclonal anti-TrpE antiserum immobilized on protein A-Sepharose beads. Immune complexes were washed, aliquoted, flash-frozen, and stored at −70° C. until mixed with mammalian cell lysates. Starved or growth factor-stimulated rat fibroblasts (~5×10$^6$) were lysed in 2 ml of lysis buffer (50 mM Hepes, pH 7.0, 150 mM NaCl, 10% glycerol, 1% Triton X-100, 1.5 mM MgCl$_2$, 1 mM EGTA, 100 mM NaF, 10 mM sodium pyrophosphate, 1 mM Na$_3$VO$_4$, 1 mM PMSF, 10 μg/ml aprotinin, 10 μg/ml leupeptin). Clarified mammalian cell lysate (1 ml) was mixed with immobilized bacterial fusion protein by gentle inversion for 90 min at 4° C. Complexes were recovered by centrifugation, washed three times with HNTG buffer (20 mM Hepes pH 7.0, 150 mM NaCl, 0.1% Triton X-100, 10% glycerol, 1 mM Na$_3$VO$_4$), and analyzed by immunoblotting with anti-P.Tyr or anti-receptor as described in Kazlauskas et al. Science 247, 1578 (1990); Koch et al. Mol. Cell. Biol. 9, 4131 (1989); and Ellis et al., Nature 343, 377 (1990). To ensure that the different TrpE fusion proteins were present in similar amounts in the immune complexes incubated with the mammalian cell lysates, duplicate samples for anti-P.Tyr and anti-EGF-R immunoblotting were probed with an anti-TrpE monoclonal antibody. Equivalent amounts of the various TrpE fusion proteins were detected.

To investigate the possibility that enzymes such as PLCγ and GAP associate directly with activated tyrosine kinase receptors by virtue of their SH2 domains, restriction sites were introduced into the complementary DNA (cDNA) for bovine PLCγ1, which allowed the precise excision of the NH$_2$-terminal and COOH-terminal SH2 domains (SH2[N] and SH2[C]), either alone or together (See detailed method described above and FIG. 7). The individual SH2 domains, or the two SH2 domains together (SH2[N+C]) were introduced into a bacterial expression vector (pATH) and expressed as TrpE fusion proteins in *Escherichia coli*. These proteins were isolated from bacterial lysates by immunoprecipitation with antibodies to TrpE (anti-TrpE) attached to Sepharose beads (See detailed method described above).

Figure 8:
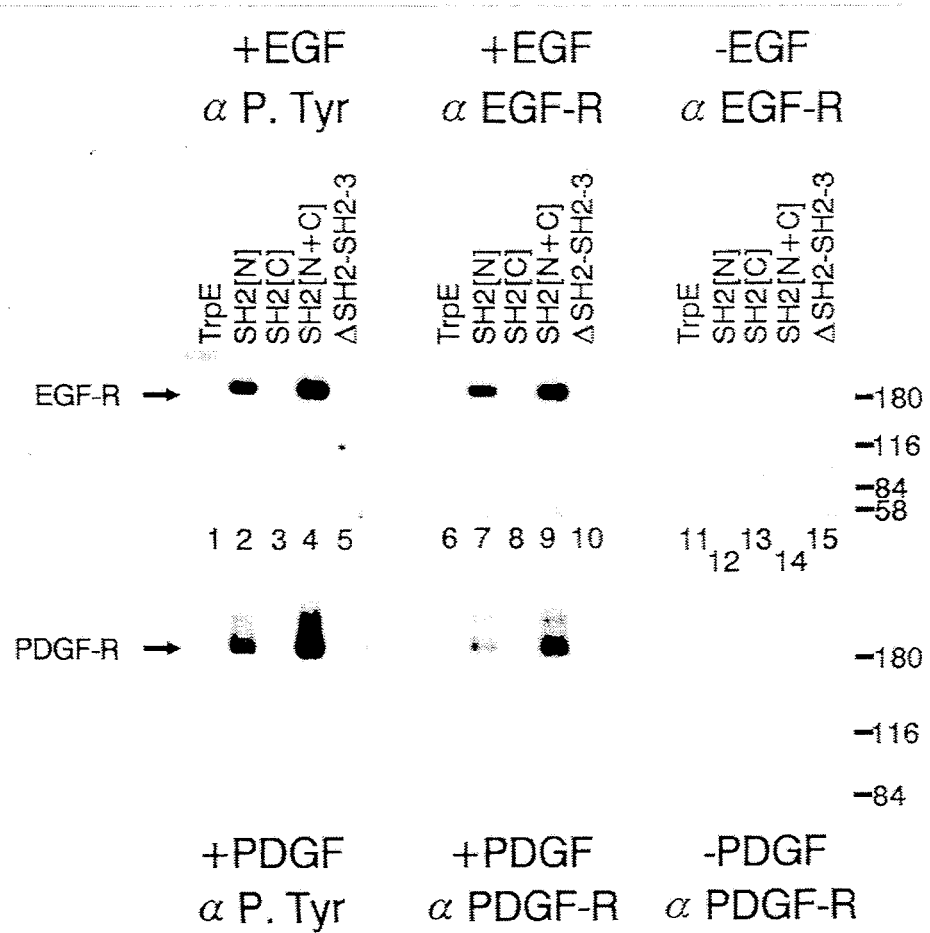
FIG. 8 shows immunoblots of immobilized TrpE fusion proteins that were mixed with lysates of Rat-1 cells overexpressing EGFR (A) and lysates from serum-starved Rat-2 cells stimulated with 75 nM BB-PDGF(B)

The immobilized bacterial proteins (parental TrpE or the indicated TrpE-PLCγ1 bacterial fusion proteins) were incubated with lysates of Rat-1 cells that overexpressed the human EGF-R (R1hER), which had been serum-starved for 48 hours (FIG. 8, lanes 11 to 15) or stimulated for 5 min at 37° C. with 80 nM EGF (FIG. 8, lanes 1 to 10). Complexes were washed, resolved on 8.25% SDS-polyacrylamide gels, and analyzed by immunoblotting with either anti(α)-P.Tyr (FIG. 8, lanes 1 to 5) or anti-EGF-R (FIG. 8, lanes 6 to 15) followed by I$^{125}$-labelled protein A. Autoradiography was for 18 hours. Immobilized TrpE or TrpE-PLCγ1 fusion proteins were also incubated with lysates from Rat-2 cells that were serum-starved for 48 hours (FIG. 8, lanes 11 to 15) or stimulated for 5 min at 37° C. with 75 nM BB-PDGF (FIG. 8, lanes 1 to 10). Samples were resolved on 6% SDS-polyacrylamide gels and analyzed by immunoblotting with either anti-P.Tyr (FIG. 8, lanes 1 to 5) or anti-PDGF-R (FIG. 8, lanes 6 to 15).

The TrpE-PLC-SH2[N] fusion protein complexed specifically with a 180-kilodalton (kD) P.Tyr-containing protein in lysates of EGF-stimulated cells. Immunoblotting of duplicate samples with antibodies to the EGF-R confirmed that this protein was the EGF-R and showed that its in vitro association with the PLCγ1 SH2[N] domain was EGF-dependent (FIG. 8). The PLCγ1 SH2[N] domain was more efficient than the SH2[C] domain in its ability to bind the EGF-R. Interestingly, the fusion protein that contained both NH$_2$- and COOH-terminal SH2 domains bound two to four-fold more EGF-R in EGF-stimulated cell lysates than could be accounted for by the two individual SH2 domains. The PLCγ1 SH2 domains therefore functioned synergistically in binding to the activated EGF-R. Very similar results were obtained for interactions of the PLCγ1 SH2 domains with the PDGF-R (FIG. 8). The PLCγ1 SH2[N] domain bound the PDGF-R in lysates of cells treated with the BB homodimeric form of PDGF but not in lysates of unstimulated cells. As observed for the EGF-R, the PLCγ1 SH2[C] domain alone was inefficient in binding activated PDGF-R, but bound synergistically with the SH2[N] domain when both domains were expressed as one bacterial protein (FIG. 8).

Within the SH2 domain, there are motifs that are particularly highly conserved. For example the NH$_2$-terminal tryptophan is invariant, and most SH2 domains start with the consensus W(Y,F)(H,F)GK (Koch et al. Mol. Cell. Biol. 9, 4131 (1989)). (Note Abbreviations for the amino acid residues are: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.) These residues may have been conserved because they are important in the interactions of SH2-containing proteins with activated growth factor receptors. A TrpE fusion protein that contained both PLCγ1 SH2 domains, with the exception that the first four residues of SH2[N] (W-F-H-G) were deleted (PLC Δ SH2-SH2-3) was expressed and its association with phosphotyrosine containing proteins in cell lysates using the techniques described above was investigated. The fusion protein showed a modest ability to bind activated EGF- or PDGF-R (FIG. 8, lanes 5 and 10) that was equivalent to the SH2[C] domain alone, indicating that the removal of the four residues weakened binding activity.

EXAMPLE 5

Binding of TryE fusion proteins that contain the GAP, Src, or Crk SH2 domains to PDGF-R in lysates of PDGF-stimulated Rat-2 cells.

The following procedure was used to investigate binding of TryE fusion proteins that contain GAP, Src, or Crk SH2 domains to PDGF-R in lysates of stimulated Rat-2 cells. Serum-starved Rat-2 cells were stimulated for 5 min at 37° C. with 75 nM BB-PDGF, lysed, and mixed with the indicated immobilized TrpE bacterial fusion proteins. Complexes were washed, resolved on 7.5% SDS-polyacrylamide gels and analyzed by immunoblotting with anti-P.Tyr (8 hour exposure) or with anti-PDGF-R (18 hour exposure).

Figure 9:
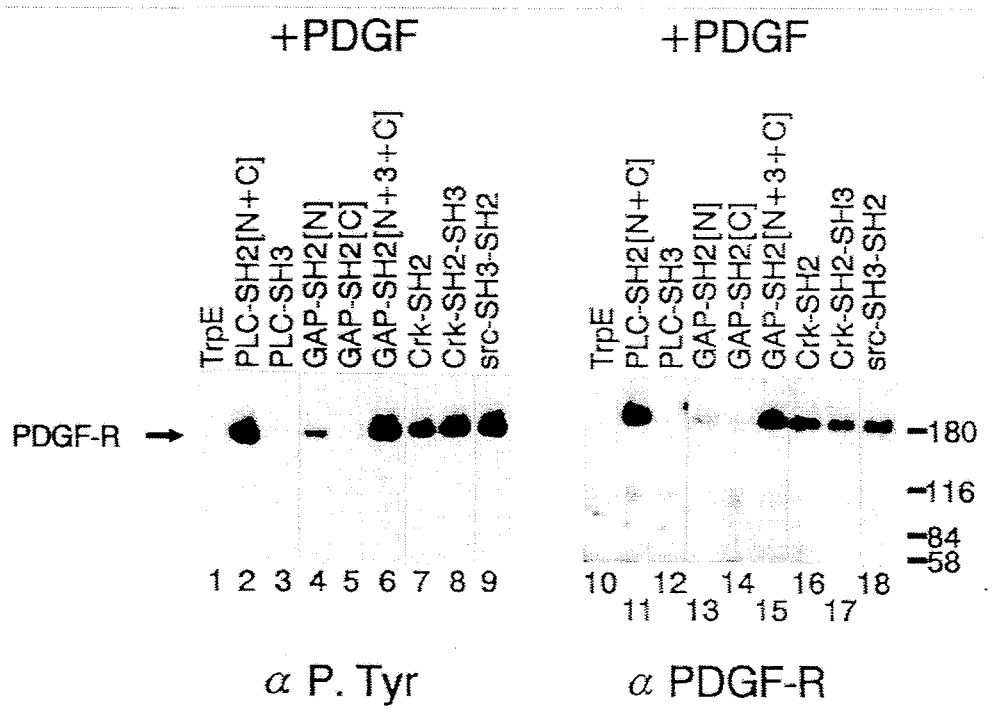
FIG. 9 shows immunoblots of immobilized TrpE fusion proteins that were mixed with serum-starved Rat-2 cells stimulated with 75 nM BB-PDGF.

Because GAP also associates with the PDGF-R, experiments were carried out using bacterial GAP SH2 sequences (see FIG. 7). The GAP SH2[N] domain bound the PDGF-R in a lysate of PDGF-stimulated cells (FIG. 9), but not in unstimulated cells. The GAP SH2[C] domain exhibited much weaker PDGF-R-binding activity. However, the two SH2 domains together (GAP-SH2[N+3+C] bound the receptor threefold more efficiently than expected from their individual binding activities (FIG. 9, lanes 4 to 6 and 13 to 15). GAP contains an SH3 domain, which intervenes between the two SH2 elements and might contribute to binding to receptors. This seems unlikely, because the PLCγ1 SH3 domain, expressed in isolation as a TrpE fusion protein, did not associate with the PDGF-R (FIG. 9).

Src-like tyrosine kinases and v-Crk also contain SH2 domains, which may bind activated receptors. Consistent with this prediction, bacterial fusion proteins that contained the SH2 domains of p60$^{src}$ or P47$^{gag-crk}$ bound PDGF-R in lysates of PDGF-stimulated Rat-2 cells (FIG. 9). p60$^{src}$ is a substrate for the PDGF-R (Ralston and Bishop, Proc. Natl. Acad. Sci. U.S.A. 82, 7845 (1985); Gould and Hunter, Mol. Cell. Biol. 8, 3345 (1988)), and recent evidence suggests that Src-like kinases are physically associated with activated PDGF-R in vivo (Kypta et al. Cell 62, 481 (1990)). The data herein imply that this interaction involves the Src SH2 domain. Whether the normal homolog of v-Crk complexes with growth factor receptors in vivo remains to be established.

EXAMPLE 6

Inhibition of in vitro binding of both PLCγ1 and GAP SH2 domains to the activated PDGF-R in Rat-2 cells that overexpress PLCγ1.

Only a minor fraction of activated PDGF-R complexes with PLCγ1 in vivo. A Rat-2 cell line was genetically modified to overexpress PLCγ1 by tenfold as compared with the endogenous enzyme (Rat-2 PLCγ1). There is a proportionate increase in the amount of PDGF-R precipitated with antibodies to PLCγ1 (anti-PLCγ1) after PDGF stimulation of Rat-2 PLCγ1 cells, in comparison with parental Rat-2 cells. If bacterial PLCγ1 SH2 domains bound to the same site(s) on the PDGF-R as did cellular PLCγ1, then overexpression of PLCγ1 should block binding of bacterial PLCγ1 SH2 domains to activated PDGF-R in vitro. To investigate this Rat-2 cells (FIG. 10, lanes 1, 2, 5 and 6) or a Rat-2 cell line that overexpressed PLCγ1 by tenfold (R2-PLCγ; lanes 3, 4, 7, 8) were stimulated with PDGF (lanes 1, 3, and 5–8) or maintained without PDGF (lanes 2 and 4). Cell lysates were mixed with immobilized TrpE-PLC-SH2[N] (lanes 1 to 4), TrpE-PLC-SH2[N+C] (lanes 5 and 7), or TrpE-GAP-SH2[N+3+C] (lanes 6 to 8). Samples were washed, separated by gel electrophoresis, and immunoblotted with anti-P.Tyr. Similar results were obtained by blotting with anti-PDGF-R.

Figure 10:
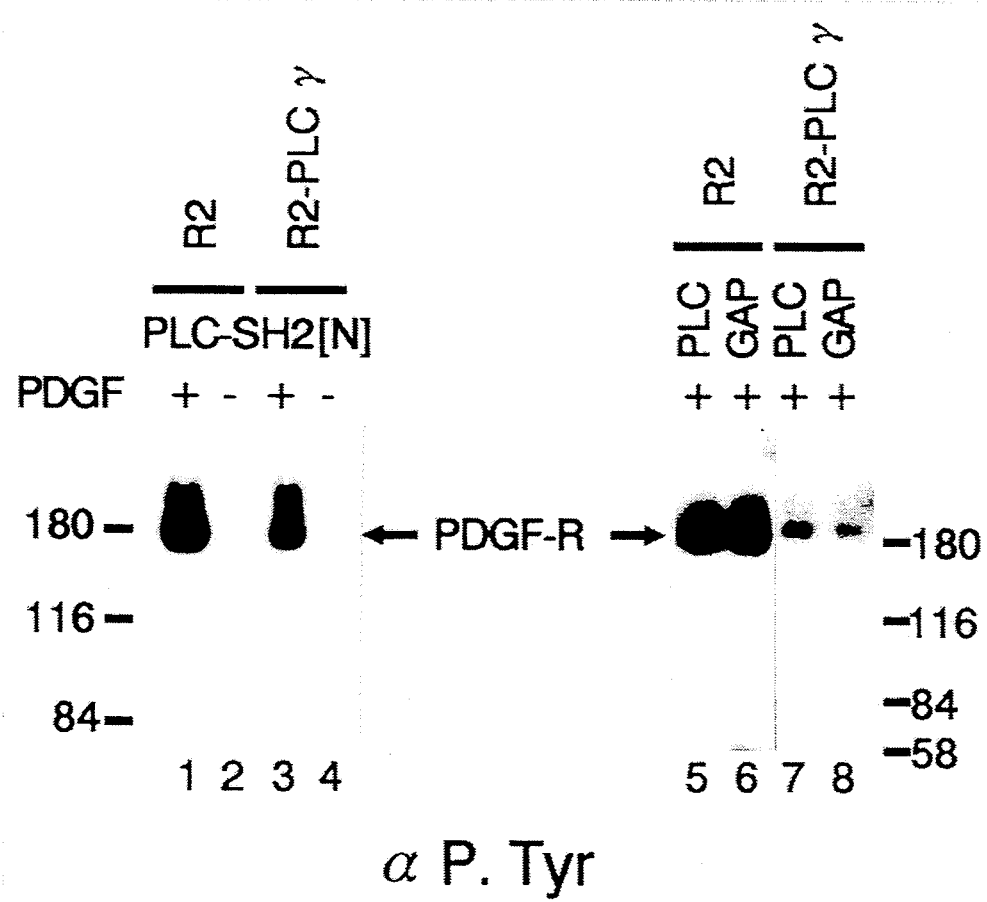
FIG. 10 shows immunoblots of immobilized TrpE fusion proteins mixed with Rat-2 cells that overexpress PLCγ1.

When the Rat-2 PLCγ1 cell line was stimulated with PDGF, lysed, and incubated with immobilized PLCγ1-SH2[N] or PLCγ1 SH2[N+C], only one-third as much PDGF-R associated with the bacterial protein, compared with the parental PDGF-stimulated Rat-2 cells (FIG. 10). Binding of TrpE-GAP-SH2 fusion protein to the PDGF-R was also reduced by overexpression of endogenous PLCγ1, suggesting that PLCγ1 and GAP compete for sites on the activated PDGF-R.

The sequences of FIG. 2 are described in the following publications which are hereby incorporated by reference:

Koch, C. A., et al. *Science*, 252, 668–674 (May 3, 1991),

Moran, et al. PNAS USA, 87, 8622–8626 (November 1990), and

Anderson, et al. *Science*, 250, 979–982 (Nov. 16, 1990).

I claim:

1. A method for assaying a medium for the presence of a substance that affects a Src homology region 2-phosphorylated ligand regulatory system comprising providing a Src homology region 2 having the amino acid sequence of the Src homology region 2 of c-Src, c-Yes, Fgr, Fyn, Lck, Lyn, Hck, Blk, c-Abl, Arg, Dabl, c-fps, Fer, PLC-γ1N, PLC-γ2N, PLC-γ1C, PLC-γ2C, GAP-N, GAP-C, p85α-N, p85β-N, p85α-C, p85β-C, Nck, Tensin, or Vav as shown in FIG. 2, and a phosphorylated ligand, the Src homology region 2 and the phosphorylated ligand being selected so that they bind to form a Src homology region 2-phosphorylated ligand complex which is capable of activating the Src homology region 2-phosphorylated ligand regulatory system, the Src homology region 2 and/or the phosphorylated ligand being present in a known concentration, and incubating with a test substance which is suspected of affecting the Src homology region 2-phosphorylated ligand regulatory system, under conditions which permit the formation of the SH2-phosphorylated ligand complex, and assaying for the SH2-phosphorylated ligand complex, free SH2-domain, or non-complexed phosphorylated ligand and comparing to a control to determine the effect of the substance.

2. A method for assaying a medium for the presence of an agonist or antagonist substance of a Src homology region 2-phosphorylated ligand regulatory system comprising providing a Src homology region 2 having the amino acid sequence of the Src homology region 2 of c-Src, c-Yes, Fgr, Fyn, Lck, Lyn, Hck, Blk, c-Abl, Arg, Dabl, c-fps, Fer, PLC-γ1N, PLC-γ2N, PLC-γ1C, PLC-γ2C, GAP-N, GAP-C, p85α-N, p85β-N, p85α-C, p85β-C, Nck, Tensin, or Vav as shown in FIG. 2, and a phosphorylated ligand, the Src homology region 2 and the phosphorylated ligand being selected so that they bind to form a Src homology region 2-phosphorylated ligand complex which is capable of activating the Src homology region 2-phosphorylated ligand regulatory system, the Src homology region 2 and/or the phosphorylated ligand being present in a known concentration, and incubating with a suspected agonist or antagonist substance, under conditions which permit the formation of the SH2-phosphorylated ligand complex, and assaying for the Src homology region 2-phosphorylated ligand complex, free Src homology region 2, or non-complexed phosphorylated ligand and comparing to a control to determine the effect of the substance.

3. A method as claimed in claim 2, wherein the phosphorylated ligand is a phosphotyrosine or phosphoserine/phosphothreonine-containing polypeptide or peptide.

4. A method as claimed in claim 3, wherein the phosphorylated ligand is a phosphotyrosine or phosphoserine/phosphothreonine-containing polypeptide or peptide.

5. A method as claimed in claim 3, wherein the phosphorylated ligand is a Src homology region 2 binding site on a transmembrane receptor with inducible protein-tyrosine kinase activity or a cytoplasmic tyrosine phosphorylated protein.

6. A method as claimed in claim 3, wherein the phosphorylated ligand is a Src homology region 2 binding site on a deregulated protein-tyrosine kinase.

7. A method as claimed in claim 4, wherein the phosphorylated ligand is a Src homology region 2 binding site on a transmembrane receptor with inducible protein-tyrosine kinase activity or a cytoplasmic tyrosine phosphorylated protein.

8. A method as claimed in claim 4, wherein the phosphorylated ligand is a Src homology region 2 binding site on a deregulated protein-tyrosine kinase.

9. A method as claimed in claim 6 or 8 wherein the deregulated tyrosine kinase is associated with thyroid cancer, breast carcinoma, stomach cancer, neuroblastoma, psoriasis, atherosclerosis, restenosis following angioplasty, allergic responses involving mast cell activation, and immunosuppression to prevent graft rejection.

10. A method as claimed in claim 1 or 2, wherein the substance assayed for affects a Src homology region 2-phosphorylated ligand regulatory system which regulates transformation pathways.

11. A pharmaceutical composition comprising an isolated Src homology region 2 having the amino acid sequence of the Src homology region 2 of c-Src, c-Yes, Fgr, Fyn, Lck, Lyn, Hck, Blk, c-Abl, Arg, Dabl, c-fps, Fer, PLC-$\gamma$1N, PLC-$\gamma$2N, PLC-$\gamma$1C, PLC-$\gamma$2C, GAP-N, GAP-C, p85$\alpha$-N, p85$\beta$-N, p85$\alpha$-C, p85$\beta$-C, Nck, Tensin, or Vav as shown in FIG. 2 for use as an agonist or antagonist of the interaction of a signalling protein with a related phosphorylated ligand.

* * * * *

UNITED STATES PATENT AND TRADEMARK OFFICE
CERTIFICATE OF CORRECTION

PATENT NO. : 5,352,660

DATED : October 4, 1994

INVENTOR(S) : Anthony J. Pawson

It is certified that error appears in the above-identified patent and that said Letters Patent is hereby corrected as shown below:

On the title page, item [75] Inventor:
Inventor's name should read "Anthony" instead of "Anthyony".

Signed and Sealed this

Twenty-second Day of August, 1995

Attest:

BRUCE LEHMAN

Attesting Officer        Commissioner of Patents and Trademarks